United States Patent
Knoesche et al.

(10) Patent No.: US 8,436,204 B2
(45) Date of Patent: May 7, 2013

(54) METHOD FOR PRODUCING ISOCYANATES

(75) Inventors: Carsten Knoesche, Niederkirchen (DE);
Eckhard Stroefer, Mannheim (DE);
Dieter Stuetzer, Dudenhofen (DE);
Bernd Sachweh, Meckenheim (DE);
Markus Linsenbuhler, Ludwigshafen (DE); Andreas Woelfert, Bad Rappenau (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 750 days.

(21) Appl. No.: 12/307,759

(22) PCT Filed: Jul. 5, 2007

(86) PCT No.: PCT/EP2007/056854
§ 371 (c)(1),
(2), (4) Date: Jan. 7, 2009

(87) PCT Pub. No.: WO2008/006775
PCT Pub. Date: Jan. 17, 2008

(65) Prior Publication Data
US 2009/0281350 A1    Nov. 12, 2009

(30) Foreign Application Priority Data
Jul. 13, 2006 (EP) .................... 06117172

(51) Int. Cl.
*C07C 263/00* (2006.01)
(52) U.S. Cl.
USPC ....................................... 560/347

(58) Field of Classification Search ........................ None
See application file for complete search history.

(56) References Cited

U.S. PATENT DOCUMENTS

| 3,401,190 A * | 9/1968 | Gude et al. ............. 560/355 |
| 3,641,094 A * | 2/1972 | Cologne-Buchheim ...... 560/347 |
| 2003/0013909 A1 | 1/2003 | Leimkuhler et al. |
| 2004/0167354 A1* | 8/2004 | Biskup et al. ............ 560/336 |
| 2005/0070734 A1 | 3/2005 | Woelfert, et al. |
| 2009/0281350 A1 | 11/2009 | Knoesche et al. |

FOREIGN PATENT DOCUMENTS

| DE | 100 26 142 | 12/2001 |
| EP | 0 570 799 | 11/1993 |
| EP | 0 593 334 | 4/1994 |
| EP | 1 275 639 | 1/2003 |
| WO | 03 045900 | 6/2003 |
| WO | 2004 062813 | 7/2004 |

OTHER PUBLICATIONS

U.S. Appl. No. 12/675,137, filed Feb. 25, 2010, Olbert, et al.
U.S. Appl. No. 12/675,187, filed Feb. 25, 2010, Olbert, et al.
U.S. Appl. No. 12/678,771, filed Mar. 18, 2010, Knoesche, et al.
U.S. Appl. No. 12/466,460, filed Apr. 21, 2009, Boehling, et al.

* cited by examiner

*Primary Examiner* — Johann Richter
*Assistant Examiner* — Jennifer C Sawyer
(74) *Attorney, Agent, or Firm* — Oblon, Spivak, McClelland, Maier & Neustadt, L.L.P.

(57) ABSTRACT

The invention provides a process for preparing isocyanates by reacting amines with phosgene, wherein the amine or a mixture of amine and a solvent is mixed in the form of an aerosol with gaseous phosgene and the amine is subsequently reacted with phosgene.

19 Claims, No Drawings

METHOD FOR PRODUCING ISOCYANATES

The invention relates to a process for preparing isocyanates by reacting amines with phosgene.

Polyisocyanates are prepared in large quantities and serve mainly as starting materials for producing polyurethanes. They are usually prepared by reacting the corresponding amines with phosgene.

Among aromatic isocyanates, methylenedi(phenyl isocyanate) (MDI) and its higher homologues and tolylene diisocyanate (TDI) have the greatest industrial importance, while among aliphatic isocyanates, hexamethylene diisocyanate (HDI) and isophorone diisocyanate (IPDI) have the greatest industrial importance.

The continuous preparation of organic isocyanates by reaction of primary organic amines with phosgene has been described many times and is carried out on a large industrial scale (see, for example, Ullmanns Enzyklopädie der Technischen Chemie, volume 7 (Polyurethane), 3rd revised edition, Carl Hanser Verlag, Munich-Vienna, p. 76ff (1993)).

The phosgenation is generally carried out in two stages. In the first stage of the phosgenation, the amine is reacted with phosgene to form carbamoyl chloride and hydrogen chloride and in a parallel reaction to form amine hydrochloride which generally precipitates as a solid because of its low solubility in the reaction mixture. The reaction between amine and phosgene is very fast, strongly exothermic and proceeds even at low temperatures. Further reactions which decrease the yield, e.g. the formation of ureas from isocyanate and amine, proceed in parallel thereto. To minimize by-products and solids formation, amine and phosgene, if appropriate in admixture with an organic solvent, therefore have to be mixed very quickly and the reaction has to be carried out with very little backmixing. The first phosgenation stage is therefore generally carried out in a mixing device, preferably in a nozzle. The second stage of the phosgenation comprises both the decomposition of the carbamoyl chloride to form the desired isocyanate and hydrogen chloride and also the phosgenation of the amine hydrochloride, which is essentially present as a solid, to form the carbamoyl chloride. The temperature of the second phosgenation stage is generally higher than that of the first. A disadvantage of this procedure is that the solids formed in the first stage of the process precipitate as coarse, possibly agglomerated solids which are difficult to phosgenate because of the operating conditions selected, and these cannot be reacted completely in the further course of the process and lead not only to decreases in yield but also to blockages and fouling. To counter this, either the temperature and thus the pressure or the residence time in the reactor have to be increased. This is generally disadvantageous for safety, technical and economic reasons. The yield of the reaction stage is determined essentially by the ratio of mixing rate and reaction rate. It has been found to be advantageous to use nozzles as described, for example, in DE 100 26 142 A1 and EP 1 275 639 as mixing device. The main ways of influencing the mixing rate are the structural configuration of the nozzle and the pressure drop realized through the nozzle. A disadvantage here is that an increasing admission pressure on the phosgene side increases the engineering and safety demands made of the pump systems and, particularly in the case of world scale plants, considerable efforts have to be made to solve the problems which occur. To minimize by-products such as ureas and their reaction products, the entire reaction has to be carried out with very little backmixing. Actual mixing devices and continuously operated reactors have an inherent degree of back-mixing which is different from zero and below which it is not possible to go. Further minimization of the by-product formation caused by backmixing is generally possible only by means of a batchwise reaction.

Recently, the preparation of isocyanates in the gas phase has become increasingly important. In these processes, the amine is present in gaseous form and is reacted with likewise gaseous phosgene. The reaction here usually proceeds above the decomposition temperature of the amine hydrochloride. The precipitation of solids in the reaction stage is thus avoided.

Such processes are known and are described, for example, in EP 570 799, EP 593 334, WO 2004/062813 or WO 03/045900.

The phosgenation of amines in the gas phase allows a considerable reduction in the solvent circulating in the process, since this can in principle be omitted in the reaction stage. In addition, higher yields than in liquid-phase phosgenation are generally achieved. Owing to the low density of the gaseous starting materials, the phosgene hold-up can be considerably reduced, and this offers significant safety advantages. Since the reaction conditions in the gas-phase phosgenation are selected so that no precipitation of amine hydrochloride can occur, the abovementioned disadvantages associated with the formation of solids which are difficult to react are avoided.

Only amines which can be brought into the gas phase with a justifiable engineering outlay can be reacted with phosgene in a gas-phase phosgenation. These are preferably the aliphatic diamines hexamethylenediamine (HDA), isophoronediamine (IPDA) and the aromatic toluenediamine (TDA). The preparation of methylenedi(phenyl isocyanate) (MDI), which is industrially always present in admixture with its higher homologues, cannot be obtained by gas-phase phosgenation since the two-ring product can be brought into the gas phase only with great difficulty and the higher homologues, i.e. products having three or more aromatic rings, cannot be brought into the gas phase at all.

It was therefore an object of the present invention to develop a process for preparing isocyanates by reacting amines with phosgene, which
- ensures a minimization of backmixing in the reactor and the associated by-product formation,
- provides an effective method of mixing amine and phosgene which realizes short mixing times at low pressure drops on the phosgene side,
- ensures that amine hydrochlorides which precipitate do not agglomerate to form large aggregates which are difficult to phosgenate and thus achieves a high space-time yield and an increase in quality, in particular in respect of impurity, the NCO content, the molecular weight distribution and the by-product spectrum of the end product.

This object has surprisingly been achieved by reacting the amines in the form of an aerosol with phosgene.

The invention accordingly provides a process for preparing isocyanates by reacting amines with phosgene, wherein the amine is reacted in the form of an aerosol with gaseous phosgene.

In the following, the droplet size distribution is the volume-weighted size distribution function. All parameters mentioned are likewise based on this distribution function.

The aerosol should have a droplet size distribution of from 10 nm to 1 mm, preferably from 100 nm to 100 μm, in particular from 0.2 to 10 μm. The droplet size distribution can be very broad or very narrow between these limits. In the ideal case, the droplet size distribution is very narrow. A measure of the breadth of the distribution is the standard deviation σ normalized on the basis of the d50 of the droplet size distribution. The d50 is the droplet size for which the cumulative distribution function reaches the value 0.5 (50%). For a very broad distribution, σ is >>1. For a narrow distribution, σ is <1, and for an ideal monodisperse distribution, σ=0.

In general, the size of the droplets should be as small as possible since this ensures a high penetration rate of the phosgene into the liquid amine-comprising phase. Furthermore, the maximum size of the precipitating amine hydrochloride particles is restricted by the droplet diameter which can be realized. For this reason, a fine aerosol is preferred to a very coarse aerosol. However, it has to be ensured that the aerosol/product produced is separated out by the downstream droplet/dust separators.

The droplet size distribution can be determined by a gravimetric measurement technique, for example the impactor or cyclone cascade measurement technique. In addition, other methods such as laser optical methods, e.g. laser scattering systems such as the Welas measurement system of Palas, Particle Doppler Anemometry (PDA), Partide Image Velocimetry (PIV), or by Scanning Mobility Particle Sizer (SMPS systems), can also be used. An overview of disperse systems and various measurement methods is given in M. Stieβ "Mechanische Verfahrenstechnik 1", Springer-Verlag, Berlin 1995, p. 4ff.

The production of the droplets and thus the aerosol can be effected by means of known aerosol production methods, in particular by means of nozzles. In one embodiment, these are single-fluid pressure nozzles including special construction types as described, for example, in the catalogue Düsen-Schlick product overview: full cone nozzles, hollow cone nozzles, centrifugal mist nozzles, etc. In this embodiment, atomization is carried out under pressure.

In a further embodiment, it is possible to use two-fluid nozzles including special construction types, if appropriate by means of atomization gas (inerts or else phosgene), (cf. catalogue Düsen-Schlick product overview: two-fluid nozzles, multifluid nozzles). In this embodiment, atomization is effected by means of an additional gas. Customary inert gases or phosgene can be used as atomizer gases.

In a further embodiment, atomization can be carried out by means of ultrasound as ultrasonic atomization or misting by means of an ultrasonic nozzle.

In a further embodiment, atomization can be carried out by means of a rotating disk, known as a rotary atomizer disk. An overview of a wide variety of forms of atomization of liquids by means of nozzles and other atomization apparatuses is given by T. Richter in "Zerstäuben von Flüssigkeiten", Expert Verlag, Renningen 2004, p. 1ff. and G. Wozniak "Zerstäubungstechnik", Springer-Verlag, Berlin 2003, pp. 57-88.

The amines can be used as pure substances or in admixture with other liquids which display inert behavior before, during and after the reaction of the amines with the phosgene. Atomization can preferably be carried out at a pressure in the reaction space ranging from 1 to 20 bar (absolute), preferably 1-10 bar, particularly preferably from 1 to 5 bar (absolute). The admission pressure upstream of the atomization device depends on the chosen method, as described above, and the fineness of the aerosol to be achieved.

When using the amines as pure substance, the atomization of the amines is preferably carried out at a temperature between the melting point and the boiling point of the amine. In particular, the atomization is carried out at the temperature corresponding to the initial temperature at which the subsequent reaction of the amine with the phosgene is carried out.

In a preferred embodiment of the process of the invention, the amine or the amine/solvent mixture is superheated under pressure before production of the aerosol so that part of the liquid vaporizes suddenly during atomization at a lower pressure and thus leads to an additional decrease in size of the droplets formed. The admission pressures here are usually in the range from 1 to 20 bar, preferably from 1 to 10 bar, absolute pressure above the reactor pressure. The admission pressure, i.e. the degree of superheating upstream of the atomization device, depends, as described above, on the desired droplet size distribution and the atomization method selected. In this embodiment of the process, the raising of the temperature and the pressure upstream of the atomization device and a sudden depressurization of the mixture to be atomized downstream of the atomization device lead to a decrease in the droplet size and a shift in the droplet size distribution towards smaller droplets.

A further possible way of decreasing the droplet size is to apply an electric field between the atomizer, in this case preferably a nozzle, and a counterelectrode, namely the electrospraying method. The electric forces which occur additionally lead to a reduction in the droplet size of the aerosol produced. Further information on the mode of action and embodiments may be found, for example, in H. Wiggers, P. Walzel, "Elektrostatisches Zerstäuben von Flüssigkeiten", Chem. Ing. Tech. 69 (1997) 1066-1073; A. G. Bailey: Electrostatic Spraying of Liquids, Res. Stud. Press Ltd Taunton, Somerset 1988; D. Michelson: Electrostatic Atomization, Adam Hilger, Bristol-N.Y. 1990.

A decrease in the droplet size can also be achieved by the above-described addition of liquids which display inert behavior before, during and after the reaction of the amines with the phosgene. Firstly, important physical properties of the amine-comprising liquid stream which influence the droplet size, e.g. the viscosity or surface tension of the stream, can be influenced in a targeted manner in this way. Secondly, an additional decrease in the droplet size can be achieved by means of vaporizing solvent in combination with the above-described method of depressurizing atomization of a superheated liquid stream. As inert compounds, preference is given to using organic solvents. Aromatic solvents, which may also be halogenated, can be used particularly advantageously here. Examples are toluene, monochlorobenzene, o- or p-dichlorobenzene, trichlorobenzene, chlorotoluenes, chloroxylenes, chloroethylbenzene, chloronaphthalenes, chlorodiphenyls, xylene, decahydronaphthalene, benzene and other mixtures. Further examples of organic solvents are methylene chloride, perchloroethylene, hexane, diethyl isophthalate, tetrahydrofuran (THF), dioxane, trichlorofluoromethane, butyl acetate and dimethylformamide (DMF).

A further possible way of optimizing the droplet size is to use classification methods. In this way, droplets which are too large can be removed prior to the reaction with phosgene. This can be achieved, for example, by installation of orifice plates or frits between the aerosol generator and the reaction zone. It is also possible to use other classification methods, for example centrifugal separators, gravity separators or electrofilters.

The liquid stream which has been separated off is preferably recirculated, i.e. returned to the starting material prior to aerosol formation.

To avoid contamination of the returned or recirculated amine with phosgene and to prevent reaction of this proportion of the liquid outside the reactor, the region of the droplet classification can be superpressurized with inert gas, for example nitrogen. This prevents entry of reaction gas, for example phosgene, into the classification space.

The reaction of the amines present as aerosol with phosgene is usually carried out at pressures of 1-20 bar (absolute), preferably 1-10 bar (absolute), particularly preferably 1-5 bar (absolute), and temperatures of 50-350° C., preferably 50-250° C., particularly preferably 90-150° C. Phosgene is mixed into the reactor in such a way that a molar excess over the amine groups of from 1:1 to 20:1, preferably from 1:1 to 10:1, particularly preferably from 1:1 to 5:1, is realized within the droplets. The reaction can be carried out in tube reactors, spray towers or loop reactors. However, it is in principle also possible to utilize other construction types which will not be listed by way of example here. If aerosol formation is not effected by means of a phosgene-operated two-fluid nozzle, gaseous phosgene has to be mixed into the aerosol after spraying of the amine or the amine/solvent mixture in such a way that very uniform mixing of the two feed streams is achieved. It is particularly important to keep the time to achievement of homogeneity as short as possible. To be able to ensure this, it is possible to employ all engineering methods with which those skilled in the art are familiar, e.g. divided introduction of the phosgene, in concurrent or in countercurrent, central, axial rotating introduction of phosgene or mixing of the feed streams in one or more nozzles such as annular gap nozzles or countercurrent nozzles. It can also be advantageous to mix the phosgene into the amine aerosol by means of slowly vaporizing and phosgene-comprising solvent droplets.

The reaction can be carried out to complete conversion into the isocyanate within the aerosol reactor. However, it can also be advantageous or necessary to carry out a partial conversion, in particular of residual amine hydrochloride, in the liquid phase in an after-reactor. The after-reactor can be a conventional type of reactor having a varying degree of backmixing, e.g. a stirred vessel, loop reactor or tube reactor. The completely or only partially reacted aerosol is separated off by means of known droplet or particle separation methods, for example filters, demisters, centrifugal separators, lamellar separators or gravity separators. A description of various droplet separators may be found in A. Bürkholz "Droplet Separation", VCH Verlagsgesellschaft, Weinheim 1989, p. 17ff. F. Löffler "Staubabscheiden", Georg Thieme Verlag, Stuttgart 1988, p. 32ff., and M. Stieβ "Mechanische Verfahrenstechnik 2", Springer-Verlag, Berlin 1997, pp. 1-53, give an overview of construction types of particle separators.

After the reaction, the mixture formed in the reaction is usually separated into isocyanate(s), inert compounds, preferably solvents, unreacted phosgene and hydrogen chloride. Small amounts of by-products which remain in the isocyanate can be separated from the desired isocyanate by means of additional rectification or crystallization.

The unreacted phosgene is usually, if appropriate after purification, recirculated and reused for the phosgenation. The hydrogen chloride formed in the reaction can, if appropriate after purification, be used for the preparation of vinyl chloride or the preparation of hydrochloric acid. It is also possible to react the hydrogen chloride with oxygen by the Deacon process to produce chlorine and recycle this to the phosgene synthesis.

As amines, it is possible to use all amines customary for the preparation of isocyanates. These are, for example, as described above, aliphatic diamines such as hexamethylenediamine (HDA), isophoronediamine (IPDA) and also the aromatic toluenediamine (TDA) and methylenedi(phenylamine) (MDA) in admixture with its higher homologues. In particular in the phosgenation of MDA, the process of the invention can be used particularly advantageously.

Compared to liquid-phase phosgenation, the process proposed here has the following substantial advantages: the backmixing of reaction product into the not yet completely reacted feed stream is minimized as a result of the spatial limitation of the liquid droplets. Very short mixing times between phosgene and amine can be realized and controlled by variation of the droplet size. The pressure drops on the phosgene side can be kept small without the mixing result being influenced significantly. The short mixing times and the low degree of backmixing lead to minimal losses in yield and high product qualities, i.e. good color numbers, low chlorine contents, high NCO numbers, an optimal molecular weight distribution, etc. The particle size of the amine hydrochlorides which precipitate is kept below a maximum value by the limiting droplet size (prevention of further agglomeration). This ensures minimal residence times for the phosgenation of amine hydrochloride and a low susceptibility of the process to fouling. In contrast to gas-phase phosgenation, amines or amine mixtures which have high boiling points and can therefore be brought into the gas phase only with great difficulty, if at all, can also be phosgenated by means of aerosol phosgenation. Furthermore, it is possible to carry out the reaction even below the boiling point of the amine. Thermally induced decreases in quality or yield can be avoided in this way. In addition, the energy-intensive vaporization of the amine or the amine mixture at high temperatures can be dispensed with.

The invention is illustrated by the following example.

EXAMPLE

MDA from the acid-catalyzed reaction of aniline with formaldehyde was atomized by means of a two-fluid nozzle (Schlick model series 970) in a spray tube reactor at a pressure of 10 bar. An MDA volume flow of 0.36 l/h (0.39 kg/h) in admixture with an MCB volume flow of 1.23 l/h (0.9 kg/h) per nozzle was achieved (1.6 l/h of fluid at 50° C.). For the atomization, an overpressure was applied to the nozzle, so that the MDA was superheated, and nitrogen under an overpressure was used as atomization gas. Overspray was retained by a perforated plate and recirculated, so that the MDA was introduced into the reactor in the form of droplets having a diameter of <10 μm. The aerosol produced in this way was reacted with phosgene injected in gaseous form in a mass ratio of 1:7.5 (2.88 kg/h at 90° C.). The MDI formed was separated off by means of a centrifugal droplet separator, discharged from the process and worked up.

The excess phosgene and the hydrogen chloride formed were discharged from the reactor and separated. The phosgene was recirculated to the process.

The invention claimed is:

1. A process for preparing isocyanates by comprising reacting amines with phosgene, wherein the amine or a mixture of amine and a solvent is mixed in the form of an aerosol with gaseous phosgene and the amine is subsequently reacted with phosgene
wherein the aerosol has a droplet size distribution of from 10 nm to 1 mm.

2. The process according to claim 1, wherein the aerosol is produced using nozzles.

3. The process according to claim 1, wherein the aerosol is produced using single-fluid pressure nozzles.

4. The process according to claim 1, wherein the aerosol is produced using two-fluid nozzles.

5. The process according to claim 1, wherein the aerosol is produced using a rotary atomizer disk.

6. The process according to claim 1, wherein the aerosol is produced using an ultrasonic nozzle.

7. The process according to claim 1, wherein the aerosol is produced using the electrospraying method.

8. The process according to claim 4, wherein said aerosol is prepared by atomization effected using an additional gas.

9. The process according to claim 5, wherein inert gases or phosgene are used as additional gas.

10. The process according to claim 1, wherein said amine or mixture of amine is at least one amine selected from the group consisting of hexamethylenediamine (HDA), isophoronediamine (IPDA), toluenediamine (TDA) and methylenedi (phenylamine) (MDA).

11. The process according to claim 1, wherein said amine is used as a pure substance.

12. The process according to claim 1, wherein said amine or mixture of amine is used together with compounds which display inert behavior during and after the reaction with the phosgene.

13. The process according to claim 1, wherein atomization is carried out at a differential pressure in the range from 1 to 20 bar absolute.

14. The process according to claim 1, wherein the reaction of the amines with phosgene is carried out at pressures of 1-20 bar (absolute).

15. The process according to claim 1, wherein the reaction of the amines with phosgene is carried out at temperatures of 50-350° C.

16. The process according to claim 1, wherein the reaction of the amines with phosgene is carried out in tube reactors, spray towers or loop reactors.

17. The process according to claim 1, wherein the aerosol has a droplet size distribution of 100 nm to 100 μm.

18. The process according to claim 1, wherein the aerosol has a droplet size distribution of 0.2 to 10 μm.

19. A process for preparing isocyanates comprising reacting amines with phosgene, wherein the amine or a mixture of amine and a solvent is mixed in the form of an aerosol with gaseous phosgene and the amine is subsequently reacted with phosgene wherein said aerosol is produced by atomizing a liquid comprising said amine or a mixture of amine.

* * * * *